US007033832B2

(12) United States Patent
Nackman et al.

(10) Patent No.: US 7,033,832 B2
(45) Date of Patent: Apr. 25, 2006

(54) ENDOTHELIAL CELL—CELL COHESION

(75) Inventors: Gary Nackman, Belle Mead, NJ (US); Ramsey Foty, Lawrenceville, NJ (US)

(73) Assignee: University of Medicine and Dentistry of New Jersey, New Brunswick, NJ (US)

(*) Notice: Subject to any disclaimer, the term of this patent is extended or adjusted under 35 U.S.C. 154(b) by 212 days.

(21) Appl. No.: 09/975,723

(22) Filed: Oct. 11, 2001

(65) Prior Publication Data

US 2003/0108529 A1 Jun. 12, 2003

Related U.S. Application Data

(60) Provisional application No. 60/243,693, filed on Oct. 27, 2000, provisional application No. 60/241,216, filed on Oct. 13, 2000.

(51) Int. Cl.
*C12N 5/00* (2006.01)
*C12N 5/06* (2006.01)
*C12N 5/08* (2006.01)

(52) U.S. Cl. ............... 435/395; 424/93.7; 435/325
(58) Field of Classification Search ............ 424/93.7; 435/395, 325
See application file for complete search history.

(56) References Cited

U.S. PATENT DOCUMENTS 5,256,141 A * 10/1993 Gencheff et al. ........... 604/501
2004/0106545 A1 * 6/2004 Blaschuk et al. ............. 514/9

FOREIGN PATENT DOCUMENTS

WO    WO 99 11814    3/1999

OTHER PUBLICATIONS

Hordijk, et al., Vascular-endothelial-cadherin modulates endothelial monolayer permeability, Journal of Cell Science, 1999, 112:1915-1923.
Li, et al., N-Cadherin-mediated Intercellular Interactions Promote Survival and Migration of Melanoma Cells, Cancer Research, 2001, 61:3819-3826.
Nebe, et al., Induction of a Physical Linkage between Integrins and the Cytoskeleton Depends on Intracellular Calcium in a Epithelial Cell Line, Experimental Cell Research, 1996, 229:100-110.
Navarro, et al., Catenin-dependent and -independent Functions of Vascular Endothelial Cadherin, The Journal of Biological Chemistry, 1995, 270:30965-30972.
Schnittlér, et al., Role of cadherins and plakoglobin in interendothelial adhesion under resting conditions and shear stress, The American Physiological Society, 1997, 363: H2396-H2400.
Ryan, et al., Tissue spreading on implantable substrates is a competitive outcome of cell—cell vs. cell-substratum adhesivity, Proceeding of the National Academy of Sciences of the United States, 2001, 98:4323-4327.
Breviaro, et al., Functional Properties of Human Vascular Endothelial Cadherin (7B4/Cadherin-5), an Endothelium-Specific Cadherin, Arterioscler Thromb Viol., 1995, 15: 1229-1239.
Monier-Gavelle and Duband, Cross Talk between Adhesion Molecules: Control of N-Cadherin Activity by Intracellular Signals Elicited by β1 and β3 Integrins in Migrating Neural Crest Cells, The Journal of Cell Biology, 1997, 137:1663-1681.
Aono, et al., p120$^{ctn}$ Acts as an Inhibitory Regulator of Cadherin Function in Colon Carcinoma Cells, The Journal of Cell Biology, 1999, 145:551-562.
Foty, et al., Surface tensions of embryonic tissues predict their mutual envelopment behavior, Development, 1996, 122:1611-1620.
Foty, et al., Dexamethasone Up-Regulates Cadherin Expression and Cohesion of HT-1080 Human Fibrosarcoma Cells[1], Cancer Research, 1998, 58:3586-3589.
Foty, et al., Measurement of Tumor Cell Cohesion and Suppression of Invasion by E- or P- Cadherin, Cancer Research, 1997, 57:5033-5036.
Lampugnani, et al., The Role of Integrins in the Maintenance of Endothelial Monolayer Integrity, The Journal of Cell Biology, 1991, 3:479-490.
Shimoyama, et al., Molecular Clonging of a Human $Ca^{2+}$-dependent Cell—Cell Adhesion Molecule Homologous to Mouse Placental Cadherin:Its Low Expression in Human Placental Tissues, The Journal of Cell Biology, 1989, 109: 1787-1794.
Kaufmann, et al., Integrin VLA-3: Ultrastructural Localization at Cell—Cell Contact Sites of Human Cell Cultures, The Journal of Cell Biology, 1989, 109:1807-1815.
Rimm, et al., Molecular Cloning Reveals Alternative Splice Forms of Human α(E)-Catenin, Biochemical and Biophysical Research Communications, 1994, 203:1691-1699.
Girard and Nerem, Endothelial cell signaling and cytosekeletal changes in response to shear stress, Frontiers Med. Biol. Engng, 1993, 5:31-36.
Telo, et al., Identification of a Novel Cadherin (Vascular Endothelial Cadherin-2) located at Intercellular junctions in Endothelial Cells. Journal of Biological Chemistry, 1998, 273:17565-17572.
Nagafuchi, Akira, Adherens junctions are composed of a cadherin-catenin complex and its associated proteins. Recently, an increasing number of novel members of adherens junctions, including membrane and PDZ proteins, have been reported. Interactions among these components in adherens junctions seem to be dynamically regulated during the formation of adherens junction complexes in epithelial cells, Current Opinion in Cell Biology, 2001, 13:600-603.

* cited by examiner

*Primary Examiner*—Ralph Gitomer
*Assistant Examiner*—Kailash C. Srivastava
(74) *Attorney, Agent, or Firm*—Klauber & Jackson

(57) ABSTRACT

Methods for stably populating solid surfaces, especially those of biomedical devices, with cells; also the resulting cell-coated surfaces.

24 Claims, 10 Drawing Sheets

HAEC    HUVEC

ENDOTHELIAL CELL—CELL COHESION

RELATED APPLICATIONS

This application claims priority of U.S. Nos. 60/241,216 filed Oct. 13, 2000 and 60/243,693 file Oct. 27, 2000 the contents of both of which are incorporated by reference.

The research leading to the present invention was supported, at least in part, by Grant ID#1 KO8 HLO4166-01 from NIH. Accordingly, the Government may have certain rights in the invention.

BACKGROUND

This invention relates to the field of coating graft surfaces with cells or inducing native cells to migrate on an implanted device or graft.

In humans, when an artificial biomaterial (prosthetic) bypass graft is placed in the circulation, the vessel's endothelial cells do not spread on the surface to completely heal the graft. Since the endothelium produces a variety of substances that inhibit blood clotting, the absence of an endothelium is problematic. This lack of endothelial healing in man is unique. Cows, pigs, dogs and primates are able to endothelialize grafts by developing a biologic lining consisting of smooth muscle cells, endothelial cells, and matrix protein on the flow lumen of the graft, shielding it from the blood. But this does not occur in man. Attempts to line prosthetic grafts prior to transplantation with human endothelial cells have not been successful because the cells don't attach well and undergo shear-induced detachment.

We have determined that human endothelial cells derived from arteries lack a certain property that renders them more prone to shear stress induced detachment. Moreover, we have identified that the surface expression of the family of proteins responsible for this behavior is substantially reduced as compared with bovine cells. The goal of this invention is to restore function to human vascular endothelial cells by modulating the presence of this factor on the cell surface. Inducing the cells to attach to each other by improving cell-cell cohesion, rather than focussing on attachment to the graft, is a goal of this invention.

SUMMARY OF THE INVENTION

In a general aspect, the invention is a method for populating a solid surface with cells by increasing the cell-to-cell cohesion of said cells. A test for cell-to-cell cohesion is the test for cell cohesivity described in Example 2. This may be done by increasing the amount of cadherin per cell. Another method for so doing comprises reducing the amount of dissociation of cadherin from the cytoskeleton of said cells. As discussed below, this may be done by various means, but in particular by reducing or eliminating the phosphorylation of a molecule associated with the adherens junction between the cells.

All aspects of this invention may be performed with any cell which can be modified to provide increased cohesivity, including cells which may be engineered for this purpose. Examples of particularly useful cells include epithelial cells, endothelial cells, in particular vascular endothelial cells, muscle cells such as smooth muscle cells, fibroblasts, mesenchymal cells, and nerve cells. Other cells which are particularly useful in this invention are cells which naturally or by engineering produce a given compound or exhibit a given behavior. For example a cell which naturally or by engineering produces heparin may be increased in cohesivity by the methods of this invention, to provide a solid surface such as a bypass graft lined with cells which produce heparin to prevent blood clotting. Cells of this invention may be obtained from any source, preferably a eukaryotic source. Human cells are preferred, but nonhuman cells are also contemplated for any use of this invention. Thus, any discussion of cells below, even if applied to a specific cell type such as a human vascular endothelial cell, may be taken to apply to nonhuman cells of the same cell type, and also to human and nonhuman cells of other cell types (with regard to discussion of specific experiments performed with specific cells in the Examples—such experiments may be performed with other cell types, but the specific results discussed apply to the cells with which the experiments were performed).

One embodiment of the invention is a method of populating a solid surface with human vascular endothelial cells, said process comprising increasing the cell-to-cell cohesion of said endothelial cells.

One aspect of the above method is populating a solid surface with human vascular endothelial cells, by reducing the amount of dissociation of cadherin from the cytoskeleton of said human vascular endothelial cells. "Reducing" means reducing the amount of dissociation to a point measurably below natural levels and includes reducing dissociation to the point of elimination. Reduction of dissociation may be accomplished by any physical, electrical, chemical or pharmacological means known in the art, including genetic engineering means of the molecules involved. In particular dissociation may be reduced by reducing or eliminating the phosphorylation of a molecule associated with the adherens junction between the human vascular endothelial cells. An example of such a molecule is β catenin. Phosphorylation of β catenin reduces cadherin association with the cytoskeleton, and methods of phosphorylating β catenin are known. It is part of this invention that phosphorylation of β catenin increases cell-cell cohesion in human vascular endothelial cells. Phosphorylation may reduced or eliminated by use of any agent known to do so, i.e. any agent which is known to modify phosphorylation, in an amount effective to reduce or eliminate phosphorylation. Examples of such agents include corticosteroids, and enzyme inhibitors such as serine-threonine kinase inhibitors, protein tyrosine kinase inhibitors, and phosphatase inhibitors. Specifically, such agents include 6-dimethylaminopurine, stuarosporine, erbstatin, herbimycin A, genestein, tyrophostins, and vanadate.

In a related aspect, the invention is a method of populating a solid surface with human vascular endothelial cells, said process comprising increasing the amount of cadherin per cell. Any cadherin (eukaryotic, preferably mammalian, more preferably human) may be used in this invention, but preferred cadherins are VE, N, E, and P cadherin. Preferably this is accomplished by increasing the number of expressible cadherin genes in the endothelial cells so as to result in the increased production of functional protein. One means of so doing is putting into the cells a gene expressibly encoding cadherin, for example by transfection, electroporation, and other known means.

In a particular aspect, the invention is a method of increasing cell-to-cell cohesion in human vascular endothelial cells. In particular embodiments of the invention, the increase in cohesion is achieved by increasing the number of cell surface molecules involved in cell-cell cohesion. In other particular embodiments, the increase in cohesion is achieved by increasing the number of functional molecules (e.g., dephosphorylated β catenin) bridging cadherins to a cytoskeleton, or otherwise reducing the amount of dissociation of cadherin from the cytoskeleton of said human vascular endothelial cells.

In a particular aspect, the invention is a method of increasing cell-to-cell cohesion, said method comprising increasing the amount of cadherin of native vascular endothelial cells.

Cadherins are glycosylated polypeptides. Virtually all multicellular organisms including, for example, those found in mammalian, avian, amphibian and teleost cells have cadherins. For purposes of implementing the present this invention, the glycosylation will take place in a human endothelial cell, but the polypeptide backbone can be that coded for by any cadherin gene, as any such gene can be transfected into human endothelial cells. It is preferred, however, that the cadherins used to effectuate the present inventions be eukaryotic cadherins, preferably mammalian cadherins, more preferably human cadherins, most preferably N-cadherins, E-cadherins, P-cadherins, and VE-cadherins. There are numerous known human cadherins.

Cadherins are recognizable because:
1) they are transmembrane proteins located at cell-to-cell junctions and are Ca2+-dependent for purposes of establishing strong, stable, intercellular bonds;
2) they react with antibodies made against various cadherin peptides, for example human VE, N-, E-, and P-cadherins.
3) they share homology to each other across species, but can differ in their extracellular domains, so as to confer specificity on individual cadherins.

One type of antibody useful in identifying cadherins is the pan-cadherin antibodies (raised against synthetic peptides containing conserved cadherin regions such as carboxy-terminal sequences). They are generally available, for example from Sigma, Mo. and were used in Example 3 below. However, any type of antibody or antibody fragment raised by any known method may be used in this context.

In another aspect, the invention is a cell-coated solid surface comprising:
  a) a solid surface; and
  b) a population of altered human vascular endothelial cells, said cells adhering to said surface, where compared to endothelial cells of equivalent origin, said altered cells (on the average) contain more cadherin per cell.
  c) alteration of native vascular endothelial cells adjacent to a vascular device to express cadherin on an endothelial cell.

Any known cadherin or fragment may be used in this invention, however preferred cadherins are VE cadherin, E cadherin, P cadherin, and N cadherin. Cadherin fragments of this invention are any part of a cadherin molecule which is effective to increase cell-cell cohesion in an assay, such as the assay of Example 2. Also part of this invention are synthetic cadherins or synthetic cadherin fragments, which can be produced and assayed by known methods.

Also contemplated for use in this invention are engineered or artificial molecules (also made by known methods) which increase cell-cell cohesivity (as measured by an assay such as that of Example 2) when inserted into a cell membrane. The artificial molecule is capable of interacting with a cell's cytoskeleton when inserted in the cell's membrane, and is capable of recognizing another surface molecule on another cell to increase cell-cell cohesivity. The surface molecule recognized by the artificial molecule may be the same artificial molecule, another artificial molecule, or a natural molecule already present on the other cell's surface. The artificial molecule is preferably a protein, proteoglycan, or peptide. In one embodiment, the artificial molecule has an intracellular, membrane, and extracellular domain. The extracellular domain is capable of tight association with another cell. The structure of such domains is well known and the artificial molecule may be designed based on such structures. Similarly it is known to design binding regions. The artificial molecule may be inserted in the cell membrane by any known means, one means being to use known techniques of genetic engineering to obtain expression by the cell of the gene encoding the artificial molecule.

In another aspect, the invention is a population of altered native vascular endothelial cells adjacent to a vascular device in a human vascular system where, compared to endothelial cells of equivalent origin, said altered cells (on the average) contain more cadherin per cell, and a population of human vascular endothelial cells adjacent to a vascular device where, compared to endothelial cells of equivalent origin, said cells have an increased number of cadherins associated with a cytoskeleton.

Two cells are of equivalent origin if they originate from the same type of tissue in the same type of organism. For example, two cells are of equivalent origin if they both originate from a human aorta, even if the aortas were in two different persons. A change in the average amount of cadherin cell per cell is a necessary and sufficient condition for a cell to be altered for purposes of the cell-coated surface inventions described herein.

Also part of this invention is a method of populating a solid surface with nonhuman endothelial cells, said cells not rejected in humans, said process comprising increasing the cell-to-cell cohesion of said endothelial cells.

Also part of this invention is a method of populating a solid surface with nonhuman endothelial cells, especially vascular endothelial cells, said cells not rejected in humans, said process comprising increasing the amount of cadherin per cell. One means for populating a solid surface with nonhuman endothelial cells is to reduce the amount of dissociation of cadherin from the cytoskeleton of said nonhuman endothelial cells. As described above, this can be accomplished by reducing or eliminating the phosphorylation of a molecule associated with the adherens junction between the nonhuman endothelial cells, in particular β catenin. Phosphorylation may reduced or eliminated by use of any agent known to do so, i.e. any agent which is known to modify phosphorylation, in an amount effective to reduce or eliminate phosphorylation. Examples of such agents include corticosteroids, and enzyme inhibitors such as serine-threonine kinase inhibitors, protein tyrosine kinase inhibitors, and phosphatase inhibitors. Specifically, such agents include 6-dimethylaminopurine, stuarosporine, erbstatin, herbimycin A, genestein, tyrophostins, and vanadate (see for example Aono, et al. J. Cell. Biol. 1999 145: 551–562 and Monier-Gavelle, et al. J. Cell Biol. 197 137: 1663–1681).

In a related aspect, the invention is a cell-coated solid surface comprising: a) a solid surface; and b) a population of altered human vascular endothelial cells, said cells adhering to said surface, where compared to endothelial cells of equivalent origin, said altered cells (on the average) contain more cadherin genes per cell, so as to cause increased expression of functional cadherin.

A solid surface of particular interest is the inner surface of a tubular graft, said inner surface defining (enclosing) an open-ended cavity that extends the length of the graft.

Another solid surface of particular interest is one within a catheter, valve, pump, or other device within or in contact with the vasculature (i.e., the arterial and/or venous system).

Other solid surfaces of interest are those of channels and chambers inside a macrochannel prosthetic delivery patch designed to store cells or pharmaceuticals for delivery via pores to adjacent tissue (or graft surface). (See, for example, U.S. Pat. No. 5,782,789, which is incorporated herein by reference.). Yet other solid surfaces of interest are those in an ex vivo device which is used outside the body, such as a heart-lung machine. In general, solid surfaces include any relevant biomedical device.

Solid surfaces of interest include both porous and non-porous surfaces. They also include living tissue, such as that of the arterial or venous system.

The methods and cell-coated surfaces of the present invention are useful for achieving better utilization of vascular grafts. They are also generally useful for any system that employs endothelial cell-coated surface susceptible to hydrodynamic shear. Such general situations include shaking containers coated with endothelial cells, continuous harvest systems for harvesting the products of endothelial cells on solid surfaces, and laminar shear devices.

Also part of this invention is a method for determining whether an agent reduces or eliminates phosphorylation of a molecule associated with the adherens junction between the human vascular endothelial cells, comprising:

a) adding said agent to a preparation of human vascular endothelial cells in the presence of a solid surface;
b) allowing said human vascular endothelial cells to populate the solid surface; and
c) determining the extent to which the human vascular endothelial cells have populated the solid surface in the presence of the agent and in the absence of the agent, and if the former is greater than the latter, thereby determining whether the agent reduces or eliminates phosphorylation of a molecule associated with the adherens junction. By this means useful agents for accomplishing the methods of this invention can be obtained.

DETAILED DESCRIPTION OF THE INVENTION

Abbreviations and Glossary

Figure 1:
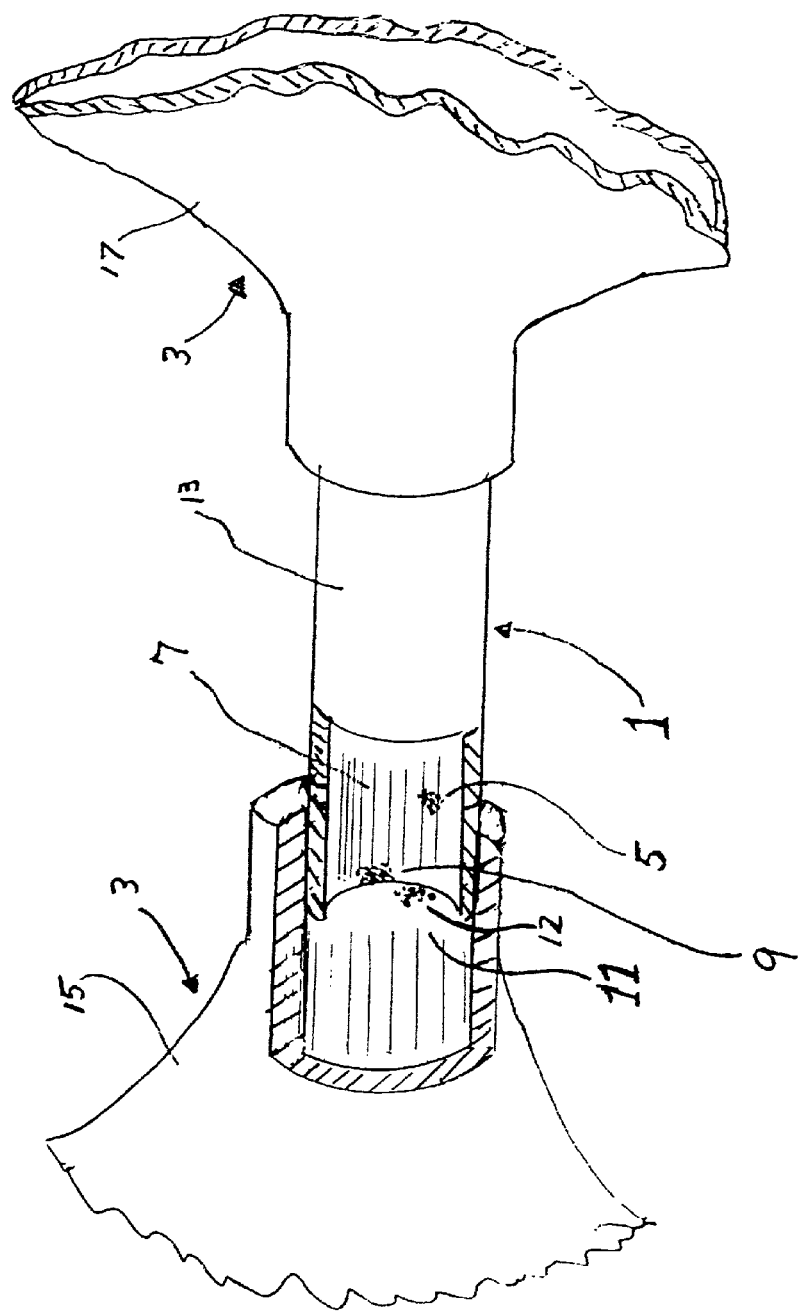
FIG. 1. Schematic, perspective view, in partial section, of a vascular graft with endothelial cells on its inner surface or in neighboring vascular tissue.

EC's stands for endothelial cells.

Endothelial cells include cells derived from either stem cells or actual blood vessels, and both those naturally occurring in a human and those cells of endothelial origin growing outside a human.

Vascular endothelial cells are those of blood carrying vessels, e.g., aortic and other arterial cells, and veins.

VE-cadherin stands for vascular endothelial cadherin.

RT-PCR refers to the Reverse Transcription—Polymerase Chain Reaction method.

A cadherin gene is any DNA sequence in a cell where that sequence can be transcribed into RNA and subsequently translated into a cadherin polypeptide.

Reducing as in reducing phosphorylation means any decrease in the level of phosphorylation from its natural levels, to the point of elimination.

Biocompatible Graft Materials

Because the basis of the invention is improved cell-to-cell cohesion, rather than improved cell-to surface adhesion, the invention can utilize a broad range of biomaterials. Such materials are non-toxic to cells, can adhere to host tissue, and are chemically stable in the environment, tubular graft or otherwise, that they are used. Preferred biomaterials will include, for example, those otherwise found to be preferred for vascular grafts. Presently preferred substrates in graft surgery are Gore-Tex® (which is e-PTFE or expanded-polytetrafluoroethylene), Dacron® (polyethylene terephthalate), urethane, silicon, metals, degradable polymers, collegen, or bioengineered blood vessels. Specific metals are metals used in stents and other implantable devices such as artificial organs.

Cadherin Amino Acid and mRNA Nucleotide Sequences

The following information on human P-cadherin (placental cadherin) was obtained from GenBank, accession number NMN_001793, which in turn refers to Y. Shimoyama et al., J. Cell Biol. 109 (4 Pt 1), 1787–1794 (1989), and appears with the GenBank disclaimer that this is a provisional reference sequence record that has not been yet subject to human review and that the final curated reference sequence may be somewhat different from this one. The amino acid sequence following "translation=" is referred to herein as SEQ ID NO:1 and the nucleotide sequence as SEQ ID NO:2.

```
                                                         (End of SEQ ID NO:1)
/translation = "MGLPRGPLASLLLLQVCWLQCAASEPCRAVFREAEVTLEAGGAE

QEPGQALGKVFMGCPGQEPALFSTDNDDFTVRNGETVQERRSLKERNPLKIFPSKRIL

RRHKRDWVVAPISVPENGKGPFPQRLNQLKSNKDRDTKIFYSITGPGADSPPEGVFAV

EKETGWLLLNKPLDREEIAKYELFGHAVSENGASVEDPMNISIIVTDQNDHKPKFTQD

TFRGSVLEGVLPGTSVMQVTATDEDDAIYTYNGVVAYSIHSQEPKDPHDLMFTIHRST

GTISVISSGLDREKVPEYTLTIQATDMDGDGSTTTAVAVVEILDANDNAPMFDPQKYE

AHVPENAVGHEVQRLTVTDLDAPNSPAWRATYLIMGGDDGDHFTITTHPESNQGILTT

RKGLDFEAKNQHTLYVEVTNEAPFVLKLPTSTATIVVHVEDVNEAPVFVPPSKVVEVQ

EGIPTGEPVCVYTAEDPDKENQKISYRILRDPAGWLAMDPDSGQVTAVGTLDREDEQF

VRNNIYEVMVLAMDNGSPPTTGTGTLLLTLIDVNDHGPVPEPRQITICNQSPVRHVLN

ITDKDLSPHTSPFQAQLTDDSDIYWTAEVNEEGDTVVLSLKKFLKQDTYDVHLSLSDH

GNKEQLTVIRATVCDCHGHVETCPGPWKGGFILPVLGAVLALLFLLLVLLLLVRKKRK

IKEPLLLPEDDTRDNVFYYGEEGGGEEDQDYDITQLHRGLEARPEVVLRNDVAPTIIP

TPMYRPRPANPDEIGNFIIENLKAANTDPTAPPYDTLLVFDYEGSGSDAASLSSLTSS

ASDQDQDYDYLNEWGSRFKKLADMYGGGEDD"
polyA_signal 3162 . . . 3167

ORIGIN                                          (And start of SEQ ID NO:2)
    1 gcggaacacc ggcccgccgt cgcggcagct gcttcacccc tctctctgca gccatggggc
   61 tccctcgtgg acctctcgcg tctctcctcc ttctccaggt ttgctggctg cagtgcgcgg
  121 cctccgagcc gtgccgggcg gtcttcaggg aggctgaagt gaccttggag gcggagggcg
  181 cggagcagga gcccggccag gcgctgggga agtattcat gggctgccct gggcaagagc
  241 cagctctgtt tagcactgat aatgatgact tcactgtgcg gaatggcgag acagtccagg
  301 aaagaaggtc actgaaggaa aggaatccat tgaagatctt cccatccaaa cgtatcttac
  361 gaagacacaa gagagattgg gtggttgctc caatatctgt ccctgaaaat ggcaagggtc
  421 ccttccccca gagactgaat cagctcaagt ctaataaaga tagagacacc aagatttct
  481 acagcatcac ggggccgggg gcagacagcc cccctgaggg tgtcttcgct gtagagaagg
  541 agacaggctg gttgttgttg aataagccac tggaccggga ggagattgcc aagtatgagc
  601 tctttggcca cgctgtgtca gagaatggtg cctcagtgga ggaccccatg aacatctcca
  661 tcatcgtgac cgaccagaat gaccacaagc ccaagtttac ccaggacacc ttccgaggga
  721 gtgtcttaga gggagtccta ccaggtactt ctgtgatgca ggtgacagcc acagatgagg
  781 atgatgccat ctacacctac aatggggtgg ttgcttactc catccatagc caagaaccaa
  841 aggacccaca cgacctcatg ttcacaattc accggagcac aggcaccatc agcgtcatct
  901 ccagtggcct ggaccgggaa aaagtccctg agtacacact gaccatccag gcccacagaca
  961 tggatgggga cggctccacc accacgcag tggcagtagt ggagatcctt gatgccaatg
 1021 acaatgctcc catgtttgac ccccagaagt acgaggccca tgtgcctgag aatgcagtgg
 1081 gccatgaggt gcagaggctg acggtcactg atctggacgc ccccaactca ccagcgtggc
 1141 gtgccaccta cctatcatg ggcggtgacg acggggacca ttttaccatc accacccacc
 1201 ctgagagcaa ccagggcatc ctgacaacca ggaagggttt ggattttgag gccaaaaacc
```

```
-continued 1261 agcacaccct gtacgttgaa gtgaccaacg aggcccttt tgtgctgaag ctcccaacct 1321 ccacagccac catagtggtc cacgtggagg atgtgaatga ggcacctgtg tttgtcccac 1381 cctccaaagt cgttgaggtc caggagggca tccccactgg ggagcctgtg tgtgtctaca 1441 ctgcagaaga ccctgacaag gagaatcaaa agatcagcta ccgcatcctg agagacccag 1501 cagggtggct agccatggac ccagacagtg ggcaggtcac agctgtgggc accctcgacc 1561 gtgaggatga gcagtttgtg aggaacaaca tctatgaagt catggtcttg gccatggaca 1621 atggaagccc tcccaccact ggcacgggaa cccttctgct aacactgatt gatgtcaacg 1681 accatggccc agtccctgag ccccgtcaga tcaccatctg caaccaaagc cctgtgcgcc 1741 acgtgctgaa catcacggac aaggacctgt ctccccacac ctcccctttc caggcccagc 1801 tcacagatga ctcagacatc tactgacgg cagaggtcaa cgaggaaggt gacacagtgg 1861 tcttgtccct gaagaagttc ctgaagcagg atacatatga cgtgcaccct tctctgtctg 1921 accatggcaa caaagagcag ctgacggtga tcagggccac tgtgtgcgac tgccatggcc 1981 atgtcgaaac ctgccctgga ccctggaaag gaggtttcat cctccctgtg ctgggggctg 2041 tcctggctct gctgttcctc ctgctggtgc tgcttttgtt ggtgagaaag aagcggaaga 2101 tcaaggagcc cctcctactc ccagaagatg acacccgtga caacgtcttc tactatggcg 2161 aagaggggg tggcgaagag gaccaggact atgacatcac ccagctccac cgaggtctgg 2221 aggccaggcc ggaggtggtt ctccgcaatg acgtggcacc aaccatcatc ccgacaccca 2281 tgtaccgtcc taggccagcc aacccagatg aaatcggcaa ctttataatt gagaacctga 2341 aggcggctaa cacagacccc acagcccgc cctacgacac cctcttggtg ttcgactatg 2401 agggcagcgg ctccgacgcc gcgtccctga gctccctcac ctcctccgcc tccgaccaag 2461 accaagatta cgattatctg aacgagtggg gcagccgctt caagaagctg gcagacatgt 2521 acggtggcgg ggaggacgac taggcggcct gcctgcaggg ctggggacca aacgtcaggc 2581 cacagagcat ctccaagggg tctcagttcc cccttcagct gaggacttcg gagcttgtca 2641 ggaagtggcc gtagcaactt ggcggagaca ggctatgagt ctgacgttag agtggttgct 2701 tccttagcct ttcaggatgg aggaatgtgg gcagtttgac ttcagcactg aaaacctctc 2761 cacctgggcc agggttgcct cagaggccaa gtttccagaa gcctcttacc tgccgtaaaa 2821 tgctcaaccc tgtgtcctgg gcctgggcct gctgtgactg acctacagtg gactttctct 2881 ctggaatgga accttcttag gcctcctggt gcaacttaat tttttttttt aatgctatct 2941 tcaaaacgtt agagaaagtt cttcaaaagt gcagcccaga gctgctgggc ccactggccg 3001 tcctgcattt ctggtttcca gaccccaatg cctcccattc ggatggatct ctgcgttttt 3061 atactgagtg tgcctaggtt gccccttatt tttttatttc cctgttgcgt tgctatagat 3121 gaagggtgag gacaatcgtg tatatgtact agaacttttt tattaaagaa a
//                                                  (End of SEQ ID NO:2)
```

Catenin Amino Acid and mRNA Nucleotide Sequences

Human catenin amino acid sequences and mRNA sequences (or corresponding cDNA seqeunces) are available in GenBank and the scientific literature. For example, D. L. Rimm et al., Biochemical and Biophysical Research Communications, vol. 203, 1691–1699 (1994), discloses cDNA and amino acid sequences for two forms of human α(E)-catenin.

Schematic Illustration of the Invention

FIG. 1 schematically illustrates the invention. A tubular graft 1 is shown joined to two portions, 15 and 17, of the same human aorta 3. The Figure is highly schematic. For example, in practice, the graft is joined to the aorta by the use of stitching (not shown) or by endovascular attachment with stents, hooks, or glue. Also the length of the tubular graft, relative to its diameter or the length of aorta overlapping the graft, may be much greater than shown in the Figure.

In the Figure, part of the aorta 3 and part of the graft 1 has been removed to better view their internal surfaces. A first population 5 of altered endothelial cells is shown on the inner surface 7 of the graft 1. Those cells originated from cells seeded on the surface 7. A second population 9 of altered endothelial cells is also shown on surface 7. The second population 9 originated from endothelial cells that make up the inner surface 11 of the aorta 3. Both populations 5 and 9 are shown as localized on a small portion of the surface 7. Preferably the population of cells completely covers the surface 7. A population 12 of altered native endothelial cells is shown as part of the inner surface of the aorta 3 adjacent to the graft device 1. All the altered cells in the Figure show increased cell-to-cell cohesivity compared to unaltered cells.

EXAMPLES

The following examples are intended to illustrate the invention, not limit it.

Example 1

To understand why humans fail to endothelialize vascular grafts, we have tested the hypothesis that endothelial cell-cell cohesion is significantly reduced in human endothelial cells and that this gives rise to the inability of human EC's to resist shear-stress induced detachment from biomaterials. We have focused our attention on cadherin-mediated cell-cell cohesion on the premise that restoring normal cadherin function in human endothelial cells will restore the ability to endothelialize vascular grafts.

Our first test of this hypothesis was to demonstrate that human aortic endothelial cells are less cohesive than bovine aortic endothelial cells. To understand why human endothelial cells fail to migrate on and undergo shear induced detachment from biomaterials, we have utilized a new model for the evaluation of the physical properties of different cell types. This model measures the cohesive binding energies of aggregates of cells. There are two general factors that must be overcome for a cell to detach from a material. One is the energy of cell-material adhesion. The other is the energy of cell-cell cohesion. We have previously shown that changes in cell aggregate cohesivity, through alteration in cadherin expression, results in a change in the ability of cells to spread on a substrate in the absence of hemodynamic forces (Reference: Foty et al. Cancer Research 58:3586–3589; Foty and Steinberg, Cancer Research 57:5033–5036; type of cell: HT-1080, LLC; (HT1080=Human Fibrosarcoma; LLC=Lewis Lung Carcinoma). Others have demonstrated as well that cells that are more cohesive spread more slowly than cells that are less cohesive. However, the cells that are more cohesive spread as a sheet of cells with increased cell-cell contact compared to the faster moving less cohesive cells (Breviario et al., Arterioscler Thromb Vasc, vol 15, pp 1229–39, 1995). This increase in cohesivity makes it more difficult for cell detachment (Applicants, data). In addition, others have shown that interfering with cohesivity leads to shear stress-induced detachment of endothelial cells from biomaterials (Schnittler et al., Am. J. Physiol., 1997, vol 273 (5Pt2): H2396–405).

The cohesivity of human and bovine aortic endothelial cells was measured by tissue surface tensiometry, (Foty, et al. Development 1996 122:1611–1620 and Foty, et al. Phys. Rev. Lett. 1994 72:2298–2301). Spherical aggregates of cells were formed by: $3 \times 10^6$ cells were trypsinized from subconfluent tissue culture plates and washed 2× in complete medium, $3 \times 10^6$ cells in 3 mls. were allowed to recover from trypsinization by shaking in a 37° water bath at 120 rpm for 4 hours. Cells were the centrifuged@950×g for 4 min. at RT in a round bottom glass tube. Pellets were then incubated O/N at 37°/5% $CO_2$. Pellets were cut into 1 $mm^2$ fragments. Fragments were placed in shaker bath for 48 hrs. Briefly, 200–300 µm diameter spherical aggregates were compressed between parallel plates in degassed $CO_2$-independent medium at 37° C. The more strongly the cells in such aggregates cohere, the greater will be the force with which they resist separation. Such aggregates also resist deformation. Using a recording electrobalance, the force exerted by the originally spherical aggregates upon the parallel plates was monitored as it decreased to a constant value following initial compression. The aggregates profile was recorded by videomicroscopy. By measuring the force of resistance to the deforming force and the geometry of the compressed aggregate, cohesivity was calculated using the Young-Laplace equation (see for example Davies and Rideal, Interface Phenomena. New York, Academic Press 1983).

The absence of cohesivity of the human aortic endothelial cells was such that aggregates cohered too weakly to allow measurement of cohesivity. However, the cohesivity of the smooth muscle cells from both species tested was measurable as noted in Table 1. The results show that these cohesivities are high and within the range of tissues, such as the embryonic chick limb bud, considered as very adhesive.

Example 2

The second methodology we employed was a functional aggregation assay. To assess function of cadherins junctions, an aggregation assay was performed comparing the formation of cellular aggregates over time among bovine aortic (BAEC), human aortic (HAEC) and umbilical vein (HUVEC) endothelial cells. All three cell types were maintained in tissue culture, then detached by trypsinization and placed in a shaking culture vessel, shaken at an initial concentration of cells of $1 \times 10^6$ cells per ml, in a solution volume of 3 ml, in a glass container in MCDB 131/2%FCS/ENDOquot Bullit kit (Clonetics). After 3 hours in shaking cultures, both BAECs and HUVECs formed cellular aggregates while HAECs demonstrated minimal aggregation, again reflecting decreased cohesivity.

The results of this Example and Example 1 demonstrate that there is a clear difference in cohesivity between human aortic endothelial cells and bovine aortic endothelial cells. In contrast, human umbilical vein endothelial cells tend to behave more like cells of non-human origin.

Example 3

The next hypothesis that we have evaluated was that the difference in cohesivity among endothelial cells of different origins could be explained by differences in cadherins present on the cell surface. Specifically, that human aortic endothelial cells would have decreased surface cadherins. All three cell types were maintained in culture. Cells were removed from the flasks by scraping and lysed for Western blotting. Experiments using a pan-cadherin antibody revealed that both BAEC and HUVEC expressed similar levels of cadherin, but HAEC expressed substantially less (50% reduction vs. BAEC, 53% vs. HUVES, ($p<0.05$ by ANOVA).

This study confirmed that the human aortic endothelial cells were deficient in cadherins relative to the more cohesive bovine and umbilical vein cells.

Example 4

To further assess the cause for decreased cohesivity, we have studied other components of the adherens junctions. Catenins are proteins that are linked to the transmembrane subunits of cadherins and maximize binding energy by allowing interaction between cadherins and the actin cytoskeleton. To identify the etiology of differences in cohesivity between human and bovine aortic ECs, $\alpha$, $\beta$, and $\gamma$ catenin expression was determined by western blotting. No differences in immunoreactivity among catenins were noted between human aortic endothelial cells and the endothelial cells from other species.

Of interest are the causes of cadherin down-regulation in human aortic endothelial cells. We have confirmed that the mRNA for VE-Cadherin is present in human aortic endothelial cells by RT-PCR. Also of interest is whether cadherin down-regulation is under transcriptional or translational control.

In one approach, one clones the gene for VE-cadherin from human endothelial cells and uses that gene to restore VE-cadherin expression in human endothelial cells with a view to increasing cohesivity and improving endothelialization of vascular grafts under shear flow conditions.

Example 5

One increases the cohesivity of human aortic endothelial cells by transfection of various cDNAs encoding several cadherins, including E-, N, P-, or VE-cadherin. One generates cell lines in which cadherin expression is under the control of an inducible promoter. The Ecdysone-Inducible Mammalian Expression System (Invitrogen) is based on the molting induction system found in Drosophila, but has been modified for inducible expression in mammalian cells. Maximal expression levels in this system are quite high, and have been reported to induce protein expression over 200 fold above basal level. In the Ecdysone-Inducible Mammalian Expression System, both subunits of a functional ecdysone receptor from Drosophila are constitutively expressed from the regulator vector pVgRXR. The ecdysone-responsive promoter (pΔHSP) which will ultimately drive the expression of the cadherin gene—is located on a second inducible expression vector. Mammalian cells are co-transfected with the inducible expression vector containing the cadherin gene along with pVgRXR by electroporation utilizing a commercially available gene transfer apparatus (Bio-Rad Gene Pulser II System). Electroporation continues to be one of the most efficient means of introducing genes into mammalian cells. Electroporation is a physical process that transiently permeabilizes eukaryotic cell membranes with an electrical pulse, thus permitting cell uptake of a wide variety of biological molecules. One optimizes the electroporation pulse for human endothelial cells by conducting experiments in which cDNA encoding green fluorescent protein (GFP) is electroporated into cells under various conditions of applied voltage and capacitance, various cDNA concentrations as well as sample volume. Once parameters are optimized, one employ similar conditions for electroporation of cadherin cDNA. Transfected cells are selected in medium containing 500 μg/ml Zeocin and 800 μg/ml G418. Stably transfected cells are placed in medium containing Ponasterone A and FACS sorted for high levels of cadherin expression.

Alternatively, one employs more conventional transfection methods allowing for efficient introduction of cadherin genes into endothelial cells. These may include calcium phosphate precipitation, lipofection, or adenovirus/retrovirus mediated infection. A somewhat less conventional approach includes use of a biolistic Gene Gun particle delivery system (BioRad). The Helios Gene Gun is a convenient, hand-held device that provides rapid and direct gene transfer into a range of targets under in vivo conditions. The unit employs an adjustable, low-pressure helium pulse to sweep DNA- or RNA-coated gold microcarriers from the inner wall of a small plastic cartridge directly into the target. Cadherin cDNAs can also be introduced in vivo by admixing with slow release polymers incorporated into the vascular graft biomaterial at the site of anastamosis.

Example 6

Figure 2:
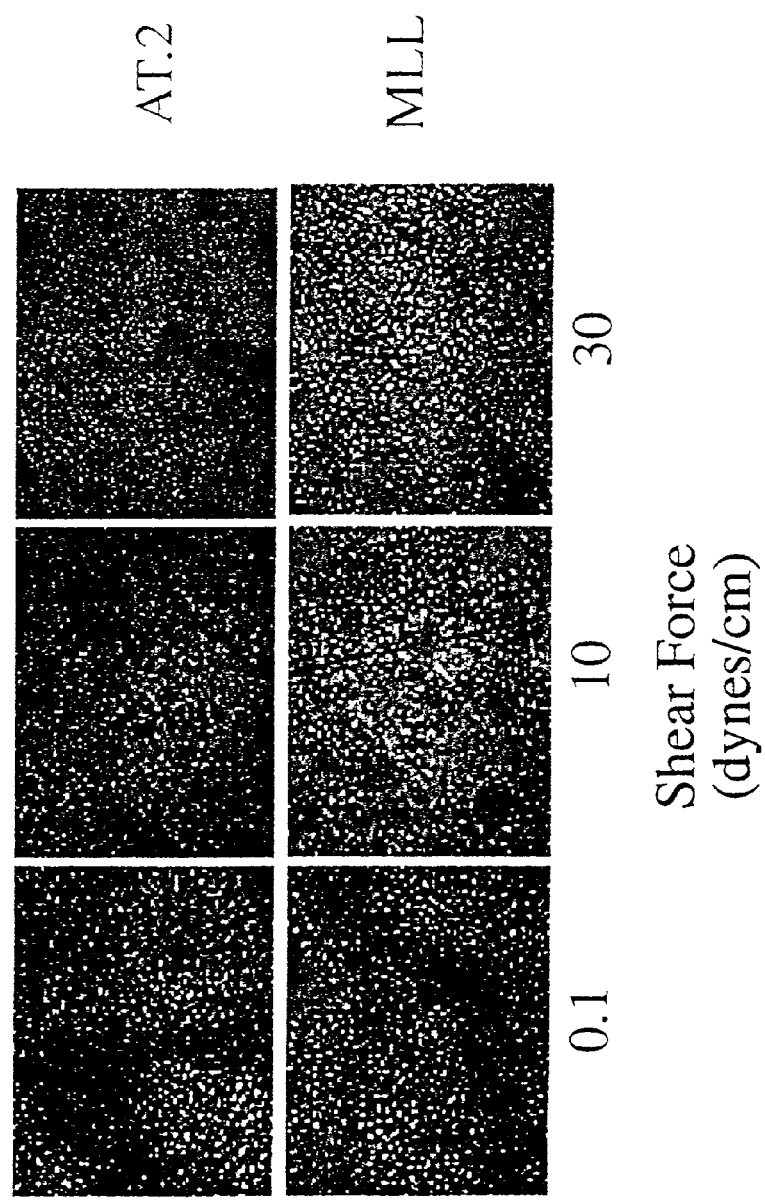
FIG. 2. Comparison of shear-induced detachment of AT.2 and MAT-LyLu from matrigel.
Figure 3:
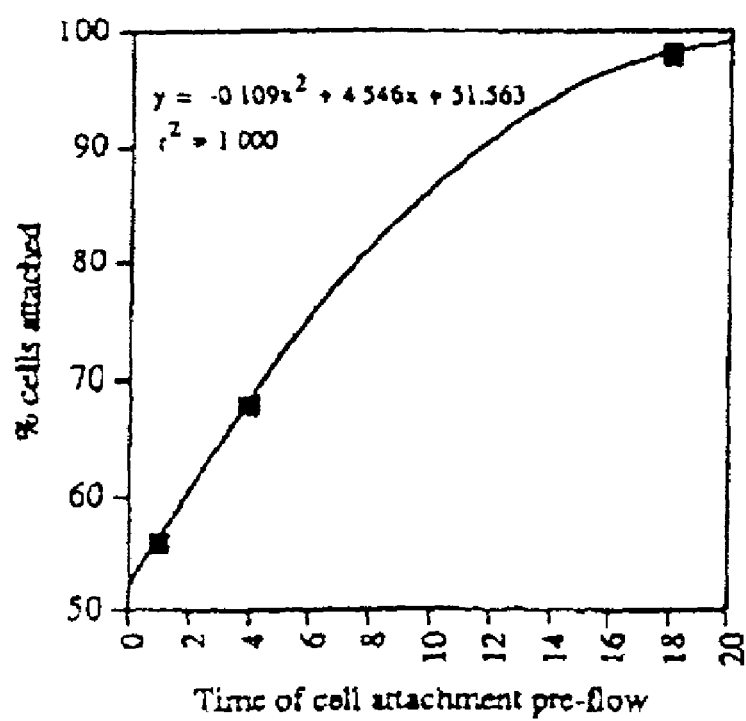
FIG. 3. Kinetics of shear-induced detachment from matrigel of MAT-LyLu cells.
Figure 4:
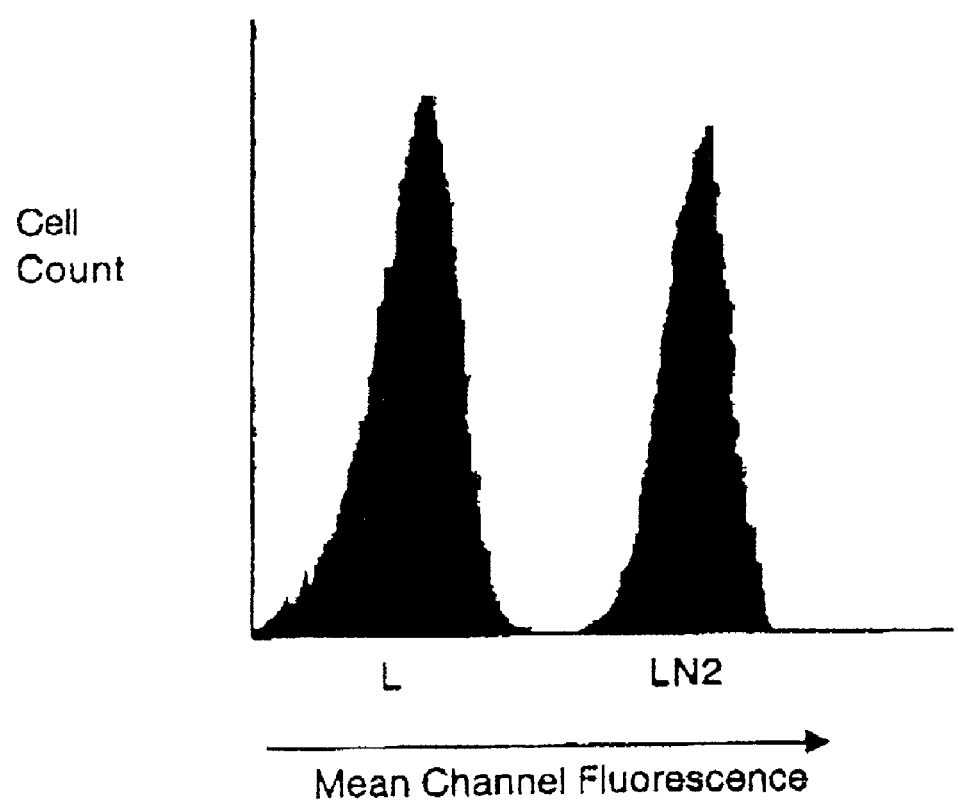
FIG. 4. FACS analysis of the L cells and genetically engineered LN2 cell line. The mean channel fluorescence (mcf) corresponding to the amount of N-cadherin expression of L cells was 0.749 which was not significantly different from background fluorescence. The mcf of the LN2 cells was 26.5.
Figure 5:
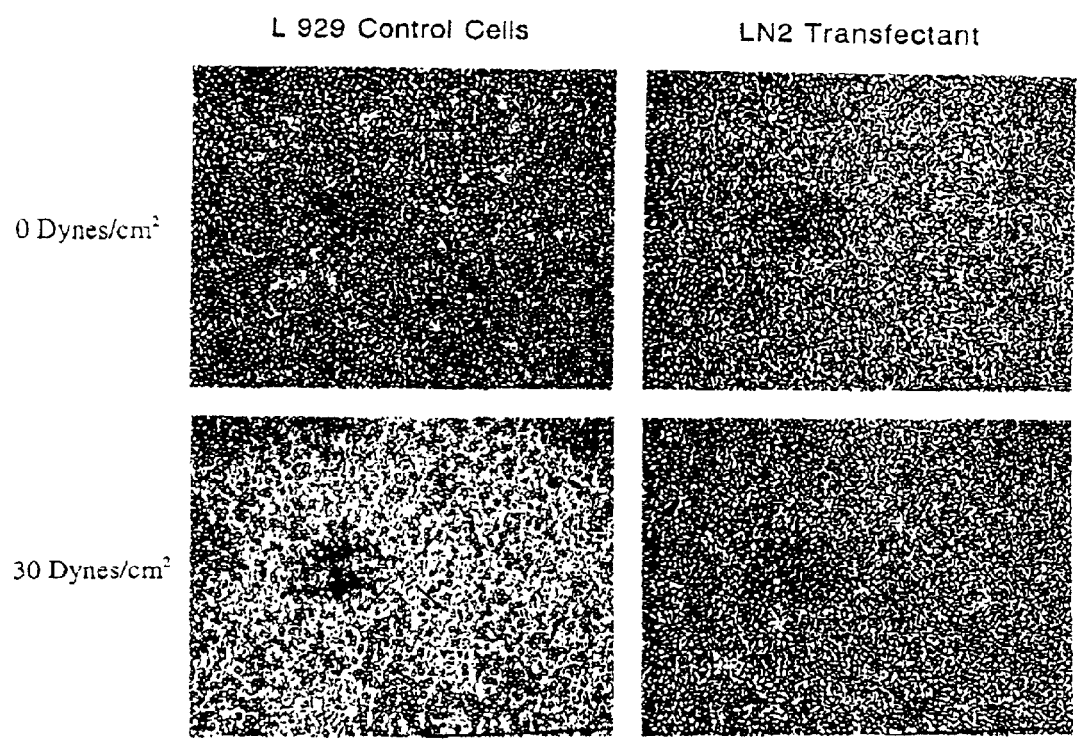
FIG. 5. Phase contract photomicrographs of the membranes were obtained of both cell types of membranes exposed to flow for 3 hr or no-flow controls. The bare area of the membranes represent area of cell detachment.
Figure 6:
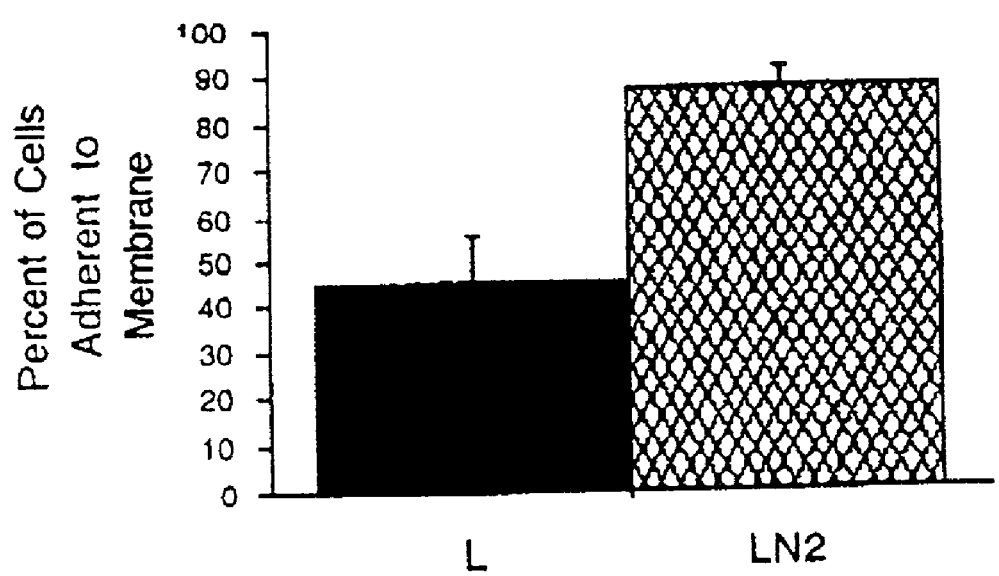
FIG. 6. Resistance to shear-induced detachment as a function of intercellular cohesivity. The more cohesive LN2 cells have greater cells remaining post-flow.

As we have demonstrated in previous publication, one can measure cell-cell cohesivity by tissue surface tensiometry. We propose that one can measure cell-substratum adhesion by shear flow induced detachment. As proof of principle, we conducted several preliminary experiments to assess the efficacy of this technique in measuring cell-substratum adhesion of two prostate cancer cell lines, In the first experiment, we compared the shear-induced detachment of the AT.2 and MAT-LyLu cell lines as a function of shear stress. In this experiment, cells were allowed to attach for 24 hours prior to the application of shear stress. We found that the less invasive, and more cohesive AT.2 cell line was better able to resist shear-induced detachment from matrigel than did the highly invasive and less cohesive MAT-LyLu (FIG. 2 shows the extent to which the surface is coated with cells after exposure to various shear forces). The next experiment asked whether we could address questions on the kinetics of cell attachment to substrate. Here we allowed MAT-LyLu cells to attach for either 1, 4 or 18 hours prior to application of shear stress then counted the number of cells still attached to substrate after 4 hours of 30 dyne/cm flow. The results showed a time-of-attachment-dependent relationship described best by a $2^{nd}$ order polynomial (FIG. 3).

TABLE 1

| Cell Type | Mean Cohesivity (dyne/cm ± SE) |
|---|---|
| Human Aortic Endothelial | <1 |
| Bovine Aortic Endothelial | 15.3 ± 3.6 |
| Human Aortic Smooth Muscle | 20.9 ± 0.4 |
| Bovine Aortic Smooth Muscle | 11.8 ± 2.9 |
| Chick Limb Bud | 20.1 ± 0.5 |

Example 7

To investigate the possible mechanisms responsible for shear induced endothelial cell detachment from biomaterials, one must consider the forces that resist this process: cell-material adhesion and cell-cell cohesion (the strength of cell-cell attachment). We have hypothesized that improved cell-cell cohesion could be an additional force that must be overcome for shear induced cell detachment to occur. We have demonstrated that differences in cell-cell cohesivity exist among endothelial cells obtained from human sort a versus bovine aorta (an example of a species that is able to endothelialize prosthetic grafts (Foty, et al. Mol. Biol. Cell. 2000:11 abstract). Human endothelial cells were noted to have significantly impaired cohesivity as compared to bovine endothelial cells. This cohesive energy is determined by the function of the adherens junctions between cells (Nagafuchi, Current Opin. Cell Biol. 2001, 13:600–603).

The adherens junction is created by the presence of transmembrane cadherin molecules linked to the actin cytoskeleton. The cadherins from adjacent cells may link to form high-energy bonds.

It has been suggested that general disturbance of cell-cell interactions could induce shear related loss of the intercellular bonds of cells (Schnittler, et al. Am. J. Physiol. 1997 273:H2396–2405). However, the specific role of cadherin mediated cell-cell cohesivity in preventing shear-induced detachment of cells from materials has not been elucidated. In this study, we tested the hypothesis that cadherin mediated cell-cell cohesivity is an independent determinant of the ability of cells to resist shear-induced detachment.

To test our hypothesis, we utilized cells that differed only in cadherin mediated cell-cell cohesivity. A mouse fibroblast cell line (L 929:ATCC) was chosen since they are a non-cohesive cell line that do not express cadherin. We genetically engineered cells to express N-cadherin. In 300 μl of serum-free RPMI 1640, 10 mM dextrose/0.1 mM dithiothreitol, $4 \times 10^6$ L cells were transferred to a 0.4 cm electroporation cuvette. Cells were transfected with 40 μg of pMiwcN chicken N-cadherin expression vector (Fujimori, et al. Development 1990 110:97–104) along with 4 μg of pZeoSV (Invitrogen, Carlsbad, Calif.) for Zeocin selection using a Bio-Rad Gene Pulser II gene transfer apparatus at 0.350 kV and 500 μF. Transfected cells were diluted 1/100 and plated into medium containing 300 μg/ml Zeocin. Resistant cells were grown to confluence, detached by trypsin/Ca2+ and stained by incubation in 10 μg/ml anti-chicken-N-Cadherin antibody (NCD2, Zymed, San Francisco, Calif.) on ice for 45 minutes. After several washes in Hanks' balanced salt solution, cells were mixed with a fluorescein isothiocyanate-conjugated secondary antibody and placed on ice for 30 min. N-cadherin-expressing cells were autocloned into 96 well plates using the Clone-Cyt Integrated Deposition System (Becton-Dickinson Immunocytometry Systems, San Jose, Calif.). Positive clones were re-analyzed by flow cytometry. Two cell lines expressing different levels of N-cadherin (Lncad-2, and Lncad-4) were propagated. These genetically engineered cells produce different levels of N-cadherin and have a linear relationship between cohesivity and cadherin expression. The LN2 cell line was used for all subsequent studies. Aggregates of LN2 cells were noted to have a measurable energy of cohesivity by tissue surface tensiometry of 1.9 dynes/cm (Ryan, et al PNAS 2001 98:4323–4327). Untransfected L cells do not form cellular aggregates and therefore precluded the use of tissue surface tensiometry.

To study shear induced detachment, we developed an assay in which approximately 50% of the non-cohesive L cells would detach during flow. Initial studies demonstrated that L-cells, despite being the least cohesive, adhered strongly to the biomaterial and resisted detachment under 30 Dynes/cm$^2$ for 24 hr. Since L cells are naturally extremely adhesive to surfaces, we needed to "passivate" the membranes prior to cell seeding to decrease integrin mediated cell adhesion. Folkman et al. had shown that a thin coating of poly HEMA at different dilutions reduces the ability of the bovine aortic endothelial cells to adhere to tissue culture plastic (Folkman and Moscona, Nature 1978 273:345–349). We dissolved 1.2 g of poly HEMA in 10 ml of 95% ethanol over night at 37 degrees. This stock solution was dissolved in 95% ethanol to obtain $2 \times 10^{-1}, 10^{-1}, 2 \times 10^{-2}, 10^{-2}, 2 \times 10^{-3}$ dilutions. The prosthetic material used as substrate was Dacron® (polyethylene terepthalate). Commercially available Dacron membranes with a pore size of 0.45 microns were used (Cyclopore membrane, Falcon cell culture insert: Becton Dickenson, Franklin Lakes, N.J.). We identified that a dilution of 1:100 resulted in 50% detachment The L and LN2 cells were plated at confluent densities ($1 \times 10^6$ cells/membrane) on the poly HEMA coated Dacron membranes. After 3 hr. the membranes were placed into a parallel plate apparatus and exposed to flow resulting in 30 dynes/cm$^2$ of shear stress for 3 hr. This apparatus has been previously described (Nackman, et al. Surgery 1998 124: 353–360). Other membranes were not exposed to shear stress to serve as no flow controls (N=3–5 membranes per call type per shear stress). Post flow, images of the remaining cells on the membranes were obtained by phase contrast microscopy. The adherent cells were released from the membrane with trypsin and manually counted with a hemocytometer. The percentage of cells remaining was determined by normalizing cells counts to the no flow controls for each cell type. ANOVA was used to determine if a statistically significant difference in resistance to shear-induced detachment among the L and LN2 cell types was present.

Analysis of L and LN2 cells by flow cytometry revealed that the LN2 cells expressed substantial amounts of N-cadherin on the cell membrane. FIG. 1 demonstrates the mean channel fluorescence of the two cell populations. The left peak represents the basal fluorescence of the L cells. The peak on the right side of the graph reveals the presence of N-cadherin on the LN2 cells.

After 3 hr. of 30 dynes/cm$^2$ of shear stress, significant numbers of L cells did detach from the membrane as compared with the more cohesive LN2 cells and the no flow controls. The post flow images revealed significantly larger area of gaps in L cell coverage of the membranes as compared with the LN2 cells (FIG. 2). Cell counts revealed that 87.4±4.4% (mean±sem) of LN2 cells remained on the membrane as compared with the no flow controls. The less cohesive L cells had significantly fewer cells present, 45.4±10.0%, P<0.05 (FIG. 3).

Adherens junctions are responsible for cell-cell cohesion and are common to many cells including endothelial cells (Navarro, et al. J. Bio. Chem. 1995 270:30965–30972). These junctions connect cells and provide them with mechanical stability. Several key proteins are know to mediate the function of adherens junctions, including the $Ca^{+2}$ dependent cadherin family, catenins, and other proteins that link to the actin cytoskeleton. This study demonstrates specifically that cadherin mediated cell-cell cohesivity has an essential role in the ability of cells to resist shearinduced detachment. The less cohesive L cells only differ from the more cohesive LN2 cells by N-cadherin expression. This proof of principle that cell-cell cohesivity affects the ability of a population of cells to resist shear induced detachment may be an important finding related to the failure of human endothelial cells to resist shear-induced detachment and to heal vascular grafts.

This study differs from other studies in the manner of evaluating the specific role of cadherin mediated cell-cell cohesion in preventing shear induced detachment. Schnittler et al. exposed human umbilical vein endothelial cells cultured on gelatin coated glass to shear stress after treatment with a high concentration of EGTA (3 nM)(Schnittler, et al.). The treatment with EGTA resulted in depletion of calcium. The investigators noted that over time calcium depletion resulted in the loss of VE-cadherin, β and Y catenin by immunostaining. This was associated with formation of gaps between cells induced by shear stress. However, cell detachment was not identified or quantified. Removal of calcium may have also altered integrin function and cell shape (Nebe, et al. Exp. CEll. Res. 1996 229:100–110). Loss of integrin function could also have affected the ability of cells to respond to shear stress (Girard and Nerem, Front. Med. Biol. Eng. 19934 5:31–36). Furthermore, integrins may also have a significant role in cell-cell attachments (Lampugnani, et al. J. Cell Biol. 1991 112:479–490 and Kaufman, et al. J. Cell Biol. 1989 109:1807–1815). Our study isolates the role of cadherin mediated cohesivity from the integrin mediated adhesivity in shear induced detachment.

To study the role of cadherin function as an independent factor in maintaining cell-cell cohesivity under shear stress, mouse fibroblast cells that express different levels of cadherin were used. In this experiment, we used an immortalized, originally non-cohesive mouse fibroblast cell line and an N-cadherin transfectant to test our proof of principle. The ideal cell type for this experiment would be to use endothelial cells obtained from human tissue. Unfortunately, no immortalized cell line of human arterial endothelial cells currently exists. We are currently in the process of generating such a line. Future studies will focus on increasing human endothelial cell cohesivity, and determining if this results in a sufficient alteration of human endothelial cell behavior to adapt to shear stress in a manner similar to endothelial cells of other species.

Example 8

Figure 7:
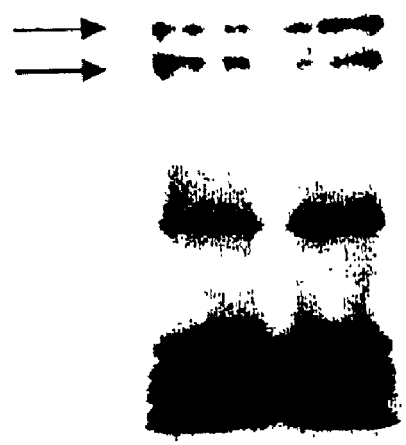
FIG. 7. VE-cadherin immunoprecipitation in human aortic vs. human umbilical vein endothelial cells. Immunoprecipitation of protein extracts from early passage human endothelial cells with an anti VE cadherin antibody followed by gel electrophoresis and immunoblotting for VE-cadherin results in a doublet. No significant difference in VE-cadherin is present.
Figure 8:
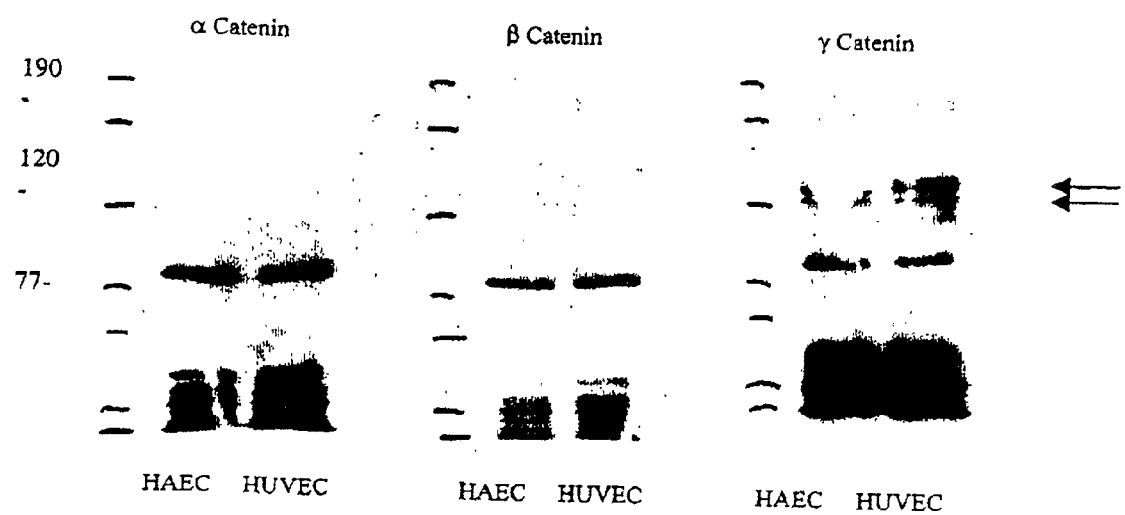
FIG. 8. VE-cadherin and $\alpha$, $\beta$, and $\gamma$ catenin coprecipitation experiments. Immunoprecipitation of protein extracts from early passage human endothelial cells with an anti VE-cadherin antibody was followed by gel electrophoresis and immunoblotting for an $\alpha$ (102 kD), $\beta$ (94 kD), and $\gamma$ (85 kD) catenin. Only $\gamma$ catenin is consistently coprecipitated.
Figure 9:
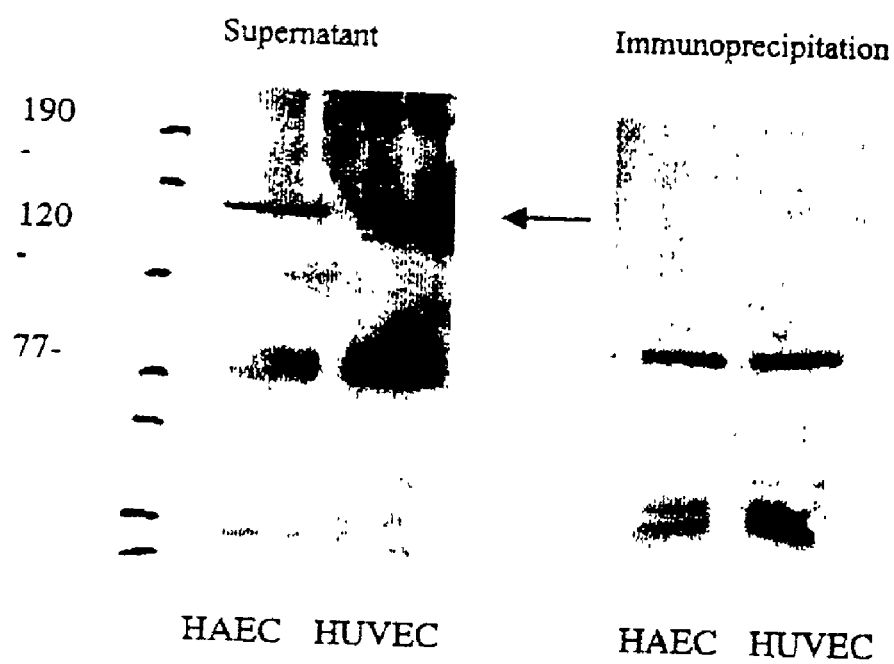
FIG. 9. VE-cadherin and $\alpha$ catenin coprecipitation vs. supernatant experiment. Immunoprecipitation of protein extracts from early passage human endothelial cells with an anti VE-cadherin antibody was followed by gel electrophoresis of the immunoprecipitated protein and the non_IP supernatant followed by immunoblotting for $\alpha$ catenin. This revealed that $\alpha$ catenin was present but not coprecipitated with VE-cadherin.
Figure 10:
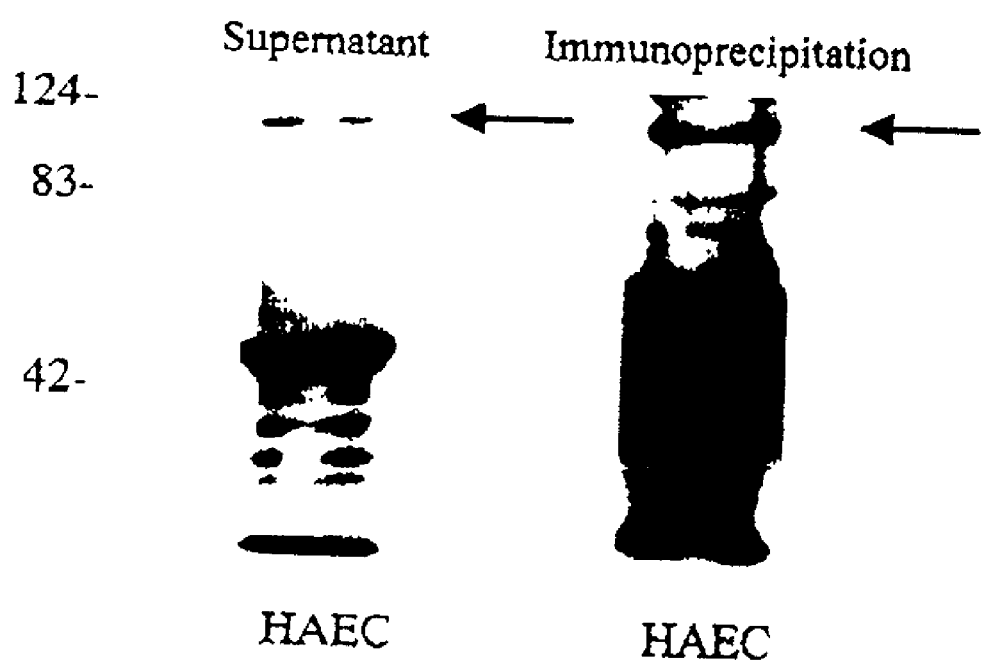
FIG. 10. All cadherins and $\alpha$, $\beta$, and $\gamma$ catenin coprecipitation experiments. Immunoprecipitation of protein extracts from human aortic endothelial cells with an anti pan-cadherin antibody was followed by gel electrophoresis of the immunoprecipitated protein and the non_IP supernatant followed by immunoblotting for $\alpha$ catenin. This revealed that $\alpha$ catenin was co-precipitated with cadherin, and also present in the non-IP supernatant.

To elucidate the mechanism responsible for failure of human endothelial cell cohesion, we continued our evaluation of differences in cadherin expression among bovine and human aortic and umbilical vein endothelial cells. We tested the hypothesis that human aortic endothelial cells would have decreased VE-cadherin present on the cell surface as compared to human umbilical vein endothelial cells. Immunoprecipitation experiments demonstrated that there were not significant differences in VE-cadherin despite the previously described 2× increase in total cadherin reactive with a pancadherin antibody (FIG. 7). This implicates that other non VE-cadherins may be significantly decreased on human aortic endothelial cells as compared with both bovine and human umbilical vein endothelial cells. We performed direct comparisons of VE-cadherin presence on porcine and human aortic endothelial cells and again found no differences.

β catenin phosphorylation is a mechanism through which the adherens junction may be rendered non-functional. After phosphorylation the a catenin complex dissociates from the cadherin. We have also tested the hypothesis that the failure of human endothelial cell cohesivity may be due to lack of function of the adherens junction. Previously we defined no difference in immunoreactive α, β, and γ catenins between human aortic, human umbilical, and bovine aortic endothelial cells. We have now demonstrated that a catenin has become disassociated from the adherens complex in human aortic and umbilical vein endothelial cells. Immunoprecipitation experiments were performed with anti VE-cadherin antibody followed by immunoblotting for α, β, and γ catenins with anti-catenin antibodies. The β and γ catenins were brought down with the VE-cadherin, however, a catenin was not (FIG. 8). The α catenin remained in the supernatant of the immunoprecipitation experiment for VE-cadherin (FIG. 9). These data support the hypothesis that the VE cadherin containing adherens junctions of human endothelial cells lack function. Whens the immunoprecipitation experiments were repeated using an anti pan-cadherin antibody rather than the anti VE cadherin antibody, α cadherin was brought down while some remained in the supernatant (FIG. 10). This implies the possible differential regulation of the adherens junctions based on type of related cadherin. Immunoprecipitation studies for β catenin followed by immunoblotting for the presence of phosphorylation reveals significantly increased phosphorylation of the β catenin of human aortic endothelial cells as compared with porcine aortic endothelial cells and human aortic smooth muscle cells.

This reveals a mechanism responsible for decreased function of the adherens junction in human endothelial cells.

What is claimed is:

1. A method for populating a solid surface of a graft or biomedical device with cells;
   wherein said method comprises seeding a first population of altered endothelial cells onto said solid surface;
   wherein said altered endothelial cells are obtained by genetic engineering techniques; and said altered endothelial cells exhibit increased cell-to-cell cohesion.

2. The method of claim 1 for populating a solid surface of a graft or biomedical device with cells, said method comprising reducing the amount of dissociation of cadherin from the cytoskeleton of said cells.

3. The method of claim 2, wherein dissociation is reduced by reducing or eliminating the phosphorylation of a molecule associated with the adherens junction between the cells.

4. The method of claim 1 for populating a solid surface of a graft or biomedical device with cells, said method comprising increasing the amount of cadherin per cell.

5. The method of claim 1 for populating a solid surface of a graft or biomedical device with cells, wherein the cells are human vascular endothelial cells, said method comprising increasing the cell-to-cell cohesion of said endothelial cells.

6. The method of claim 5 for populating a solid surface of a graft or biomedical device with human vascular endothelial cells, said method comprising reducing the amount of dissociation of cadherin from the cytoskeleton of said human vascular endothelial cells.

7. The method of claim 6, wherein said dissociation is reduced by reducing or eliminating the phosphorylation of a molecule associated with the adherens junction between the human vascular endothelial cells.

8. The method of claim 7, wherein the molecule associated with the adherens junction is β catenin.

9. The method of claim 7, wherein phosphorylation is reduced or eliminated by applying an amount of an agent that is known to modify said phosphorylation to reduce or eliminate said phosphorylation.

10. The method of claim 5 for populating a solid surface of a graft or biomedical device with human vascular endothelial cells, said process comprising increasing the amount of cadherin per cell.

11. The method of claim 10, wherein the amount of cadherin per cell is increased by increasing the number of expressible cadherin genes in the endothelial cells.

12. The method of claim 10, wherein the increased cadherin comprises a eukaryotic cadherin polypeptide.

13. The method of claim 12, wherein the eukaryotic cadherin polypeptide is a mammalian cadherin polypeptide.

14. The method of claim 13, wherein the mammalian cadherin polypeptide is a human cadherin polypeptide.

15. The method of claim 14, wherein the human cadherin polypeptide is selected from the group consisting of an N-cadherin polypeptide, a P-cadherin polypeptide, an E-cadherin polypeptide, and a VE-cadherin polypeptide.

16. A method to increase cell-to-cell cohesion in human vascular endothelial cells on a graft or biomedical device.

17. The method of claim 16 comprising increasing the amount of cadherin per cell in vascular endothelial cells.

18. The method of claim 16, wherein the increase in cohesion is achieved by increasing the number of cell surface molecules involved in cell-to-cell cohesion.

19. The method of claim 19, comprising reducing the amount of dissociation of cadherin from the cytoskeleton of said human vascular endothetial cells.

20. The method of claim 19, wherein the increase in cohesion is achieved by increasing the number of molecules that bridge cadherin to the cytoskeleton.

21. The method of claim 1, wherein said graft or biomedical device is in contact with an arterial and/or venous system.

22. The method of claim 1, wherein said solid surface is a surface of a graft.

23. The method of claim 22, wherein said graft is a vascular graft.

24. The method of claim 22, wherein said graft is a tubular graft.

* * * * *

SEQUENCE LISTING

```
<160> NUMBER OF SEQ ID NOS: 2

<210> SEQ ID NO 1
<211> LENGTH: 829
<212> TYPE: PRT
<213> ORGANISM: Homo sapiens

<400> SEQUENCE: 1

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
        35                  40                  45

Gln Ala Leu Gly Lys Val Phe Met Gly Cys Pro Gly Gln Glu Pro Ala
    50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95
```

```
Pro Ser Lys Arg Ile Leu Arg Arg His Lys Arg Asp Trp Val Val Ala
        100                 105                 110
Pro Ile Ser Val Pro Glu Asn Gly Lys Gly Pro Phe Pro Gln Arg Leu
        115                 120                 125
Asn Gln Leu Lys Ser Asn Lys Asp Arg Asp Thr Lys Ile Phe Tyr Ser
        130                 135                 140
Ile Thr Gly Pro Gly Ala Asp Ser Pro Glu Gly Val Phe Ala Val
145                 150                 155                 160
Glu Lys Glu Thr Gly Trp Leu Leu Asn Lys Pro Leu Asp Arg Glu
                165                 170                 175
Glu Ile Ala Lys Tyr Glu Leu Phe Gly His Ala Val Ser Glu Asn Gly
                180                 185                 190
Ala Ser Val Glu Asp Pro Met Asn Ile Ser Ile Val Thr Asp Gln
        195                 200                 205
Asn Asp His Lys Pro Lys Phe Thr Gln Asp Thr Phe Arg Gly Ser Val
        210                 215                 220
Leu Glu Gly Val Leu Pro Gly Thr Ser Val Met Gln Val Thr Ala Thr
225                 230                 235                 240
Asp Glu Asp Asp Ala Ile Tyr Thr Tyr Asn Gly Val Val Ala Tyr Ser
                245                 250                 255
Ile His Ser Gln Glu Pro Lys Asp Pro His Asp Leu Met Phe Thr Ile
                260                 265                 270
His Arg Ser Thr Gly Thr Ile Ser Val Ile Ser Ser Gly Leu Asp Arg
        275                 280                 285
Glu Lys Val Pro Glu Tyr Thr Leu Thr Ile Gln Ala Thr Asp Met Asp
        290                 295                 300
Gly Asp Gly Ser Thr Thr Thr Ala Val Ala Val Val Glu Ile Leu Asp
305                 310                 315                 320
Ala Asn Asp Asn Ala Pro Met Phe Asp Pro Gln Lys Tyr Glu Ala His
                325                 330                 335
Val Pro Glu Asn Ala Val Gly His Glu Val Gln Arg Leu Thr Val Thr
                340                 345                 350
Asp Leu Asp Ala Pro Asn Ser Pro Ala Trp Arg Ala Thr Tyr Leu Ile
        355                 360                 365
Met Gly Gly Asp Asp Gly Asp His Phe Thr Ile Thr Thr His Pro Glu
        370                 375                 380
Ser Asn Gln Gly Ile Leu Thr Thr Arg Lys Gly Leu Asp Phe Glu Ala
385                 390                 395                 400
Lys Asn Gln His Thr Leu Tyr Val Glu Val Thr Asn Glu Ala Pro Phe
                405                 410                 415
Val Leu Lys Leu Pro Thr Ser Thr Ala Thr Ile Val Val His Val Glu
                420                 425                 430
Asp Val Asn Glu Ala Pro Val Phe Val Pro Pro Ser Lys Val Val Glu
        435                 440                 445
Val Gln Glu Gly Ile Pro Thr Gly Glu Pro Val Cys Val Tyr Thr Ala
        450                 455                 460
Glu Asp Pro Asp Lys Glu Asn Gln Lys Ile Ser Tyr Arg Ile Leu Arg
465                 470                 475                 480
Asp Pro Ala Gly Trp Leu Ala Met Asp Pro Asp Ser Gly Gln Val Thr
                485                 490                 495
Ala Val Gly Thr Leu Asp Arg Glu Asp Glu Gln Phe Val Arg Asn Asn
        500                 505                 510
```

-continued

```
Ile Tyr Glu Val Met Val Leu Ala Met Asp Asn Gly Ser Pro Pro Thr
        515                 520                 525
Thr Gly Thr Gly Thr Leu Leu Leu Thr Leu Ile Asp Val Asn Asp His
        530                 535                 540
Gly Pro Val Pro Glu Pro Arg Gln Ile Thr Ile Cys Asn Gln Ser Pro
545                 550                 555                 560
Val Arg His Val Leu Asn Ile Thr Asp Lys Asp Leu Ser Pro His Thr
                565                 570                 575
Ser Pro Phe Gln Ala Gln Leu Thr Asp Asp Ser Asp Ile Tyr Trp Thr
            580                 585                 590
Ala Glu Val Asn Glu Glu Gly Asp Thr Val Val Leu Ser Leu Lys Lys
        595                 600                 605
Phe Leu Lys Gln Asp Thr Tyr Asp Val His Leu Ser Leu Ser Asp His
    610                 615                 620
Gly Asn Lys Glu Gln Leu Thr Val Ile Arg Ala Thr Val Cys Asp Cys
625                 630                 635                 640
His Gly His Val Glu Thr Cys Pro Gly Pro Trp Lys Gly Gly Phe Ile
                645                 650                 655
Leu Pro Val Leu Gly Ala Val Leu Ala Leu Leu Phe Leu Leu Leu Val
            660                 665                 670
Leu Leu Leu Leu Val Arg Lys Lys Arg Lys Ile Lys Glu Pro Leu Leu
        675                 680                 685
Leu Pro Glu Asp Asp Thr Arg Asp Asn Val Phe Tyr Tyr Gly Glu Glu
    690                 695                 700
Gly Gly Gly Glu Glu Asp Gln Asp Tyr Asp Ile Thr Gln Leu His Arg
705                 710                 715                 720
Gly Leu Glu Ala Arg Pro Glu Val Val Leu Arg Asn Asp Val Ala Pro
                725                 730                 735
Thr Ile Ile Pro Thr Pro Met Tyr Arg Pro Arg Pro Ala Asn Pro Asp
            740                 745                 750
Glu Ile Gly Asn Phe Ile Ile Glu Asn Leu Lys Ala Ala Asn Thr Asp
        755                 760                 765
Pro Thr Ala Pro Pro Tyr Asp Thr Leu Leu Val Phe Asp Tyr Glu Gly
    770                 775                 780
Ser Gly Ser Asp Ala Ala Ser Leu Ser Ser Leu Thr Ser Ser Ala Ser
785                 790                 795                 800
Asp Gln Asp Gln Asp Tyr Asp Tyr Leu Asn Glu Trp Gly Ser Arg Phe
                805                 810                 815
Lys Lys Leu Ala Asp Met Tyr Gly Gly Gly Glu Asp Asp
            820                 825
```

<210> SEQ ID NO 2
<211> LENGTH: 3170
<212> TYPE: DNA
<213> ORGANISM: Homo sapiens

<400> SEQUENCE: 2

```
gcggaacacc ggcccgccgt cgcggcagct gcttcacccc tctctctgca gccatggggc    60
tccctcgtgg acctctcgcg tctctcctcc ttctccaggt ttgctggctg cagtgcgcgg   120
cctccgagcc gtgccgggcg gtcttcaggg aggctgaagt gaccttggag gcggaggcg   180 cggagcagga gcccggccag gcgctgggga agtattcat gggctgccct gggcaagagc   240
cagctctgtt tagcactgat aatgatgact tcactgtgcg gaatggcgag acagtccagg   300
aaagaaggtc actgaaggaa aggaatccat tgaagatctt cccatccaaa cgtatcttac   360
```

```
gaagacacaa gagagattgg gtggttgctc caatatctgt ccctgaaaat ggcaagggtc    420 ccttcccca gagactgaat cagctcaagt ctaataaaga tagagacacc aagattttct     480
acagcatcac ggggccgggg gcagacagcc cccctgaggg tgtcttcgct gtagagaagg    540
agacaggctg gttgttgttg aataagccac tggaccggga ggagattgcc aagtatgagc    600
tctttggcca cgctgtgtca gagaatggtg cctcagtgga ggaccccatg aacatctcca    660
tcatcgtgac cgaccagaat gaccacaagc ccaagtttac ccaggacacc ttccgaggga    720
gtgtcttaga gggagtccta ccaggtactt ctgtgatgca ggtgacagcc acagatgagg    780
atgatgccat ctacacctac aatggggtgg ttgcttactc catccatagc caagaaccaa    840
aggacccaca cgacctcatg ttcacaattc accggagcac aggcaccatc agcgtcatct    900
ccagtggcct ggaccgggaa aaagtccctg agtacacact gaccatccag gccacagaca    960
tggatgggga cggctccacc accacggcag tggcagtagt ggagatcctt gatgccaatg   1020
acaatgctcc catgtttgac ccccagaagt acgaggccca tgtgcctgag aatgcagtgg   1080
gccatgaggt gcagaggctg acggtcactg atctggacgc ccccaactca ccagcgtggc   1140
gtgccaccta ccttatcatg ggcggtgacg acggggacca ttttaccatc accacccacc   1200
ctgagagcaa ccagggcatc ctgacaacca ggaagggttt ggattttgag gccaaaaacc   1260
agcacaccct gtacgttgaa gtgaccaacg aggccccttt tgtgctgaag ctcccaacct   1320
ccacagccac catagtggtc cacgtggagg atgtgaatga ggcacctgtg tttgtcccac   1380
cctccaaagt cgttgaggtc caggagggca tccccactgg ggagcctgtg tgtgtctaca   1440
ctgcagaaga ccctgacaag gagaatcaaa agatcagcta ccgcatcctg agagacccag   1500
cagggtggct agccatggac ccagacagtg ggcaggtcac agctgtgggc accctcgacc   1560
gtgaggatga gcagtttgtg aggaacaaca tctatgaagt catggtcttg gccatggaca   1620
atggaagccc tcccaccact ggcacgggaa cccttctgct aacactgatt gatgtcaacg   1680
accatggccc agtccctgag ccccgtcaga tcaccatctg caaccaaagc cctgtgcgcc   1740
acgtgctgaa catcacggac aaggacctgt ctcccacac ctccccttc caggcccagc   1800 tcacagatga ctcagacatc tactggacgg cagaggtcaa cgaggaaggt gacacagtgg   1860
tcttgtccct gaagaagttc ctgaagcagg atacatatga cgtgcacctt tctctgtctg   1920
accatggcaa caaagagcag ctgacggtga tcagggccac tgtgtgcgac tgccatggcc   1980
atgtcgaaac ctgccctgga ccctggaaag gaggtttcat cctccctgtg ctggggctg    2040 tcctggctct gctgttcctc ctgctggtgc tgcttttgtt ggtgagaaag aagcggaaga   2100
tcaaggagcc cctcctactc ccagaagatg acacccgtga caacgtcttc tactatggcg   2160 aagaggggg tggcgaagag gaccaggact atgacatcac ccagctccac cgaggtctgg   2220
aggccaggcc ggaggtggtt ctccgcaatg acgtggcacc aaccatcatc ccgacaccca   2280
tgtaccgtcc taggccagcc aacccagatg aaatcggcaa ctttataatt gagaacctga   2340
aggcggctaa cacagacccc cacagccccg cctacgacac cctcttggtg ttcgactatg   2400
agggcagcgg ctccgacgcc gcgtccctga gctccctcac ctcctccgcc tccgaccaag   2460
accaagatta cgattatctg aacgagtggg gcagccgctt caagaagctg gcagacatgt   2520
acggtggcgg ggaggacgac taggcggcct gcctgcaggg ctggggacca aacgtcaggc   2580
cacagagcat ctccaagggg tctcagttcc cccttcagct gaggacttcg gagcttgtca   2640
ggaagtggcc gtagcaactt ggcggagaca ggctatgagt ctgacgttag agtggttgct   2700
```

-continued

```
tccttagcct ttcaggatgg aggaatgtgg gcagtttgac ttcagcactg aaaacctctc  2760
cacctgggcc agggttgcct cagaggccaa gtttccagaa gcctcttacc tgccgtaaaa  2820
tgctcaaccc tgtgtcctgg gcctgggcct gctgtgactg acctacagtg gactttctct  2880
ctggaatgga accttcttag gcctcctggt gcaacttaat ttttttttt aatgctatct   2940 tcaaaacgtt agagaaagtt cttcaaaagt gcagcccaga gctgctgggc ccactggccg  3000
tcctgcattt ctggtttcca gaccccaatg cctcccattc ggatggatct ctgcgttttt  3060
atactgagtg tgcctaggtt gccccttatt ttttattttc cctgttgcgt tgctatagat  3120
aagggtgagg acaatcgtgt atatgtacta gaactttttt attaaagaaa              3170
```